(12) United States Patent
Grant et al.

(10) Patent No.: US 11,471,622 B2
(45) Date of Patent: Oct. 18, 2022

(54) INHALER WITH SWIRL END PLUG

(71) Applicant: PHILIP MORRIS PRODUCTS S.A., Neuchâtel (CH)

(72) Inventors: Christopher John Grant, Neuchâtel (CH); Gerard Zuber, Neuchâtel (CH); Daniele Sanna, Marin-Epagnier (CH); Gianluca Sechi, Lausanne (CH); Judith Waller, Ostersund (SE); Niki Meloncelli, Castel Maggiore (IT)

(73) Assignee: Philip Morris Products S.A., Neuchatel (CH)

( * ) Notice: Subject to any disclaimer, the term of this patent is extended or adjusted under 35 U.S.C. 154(b) by 231 days.

(21) Appl. No.: 16/464,789

(22) PCT Filed: Nov. 17, 2017

(86) PCT No.: PCT/IB2017/057219
§ 371 (c)(1),
(2) Date: May 29, 2019

(87) PCT Pub. No.: WO2018/100461
PCT Pub. Date: Jun. 7, 2018

(65) Prior Publication Data
US 2019/0307976 A1    Oct. 10, 2019

(30) Foreign Application Priority Data
Nov. 30, 2016 (EP) ...................................... 16201579

(51) Int. Cl.
*A61M 15/00* (2006.01)
*A61M 15/06* (2006.01)
(Continued)

(52) U.S. Cl.
CPC ............ *A61M 15/0028* (2013.01); *A24D 3/17* (2020.01); *A24F 42/20* (2020.01); *A24F 42/60* (2020.01);
(Continued)

(58) Field of Classification Search
CPC .... A24F 47/002; A24F 47/0008; A24F 42/20; A24F 42/60; A24F 40/00; A24F 40/05;
(Continued)

(56) References Cited

U.S. PATENT DOCUMENTS 3,991,761 A    11/1976 Cocozza
4,069,819 A *   1/1978 Valentini ........... A61M 15/0033
                                                    604/131
(Continued)

FOREIGN PATENT DOCUMENTS

EA            15651 B1    10/2011
GB          2539176 A    12/2016
(Continued)

OTHER PUBLICATIONS

Russian Office Action and Search Report for RU Application No. 2019116593 dated Feb. 25, 2021; 14 pgs. including English Translation.
(Continued)

*Primary Examiner* — Alex B Efta
(74) *Attorney, Agent, or Firm* — Mueting Raasch Group

(57) ABSTRACT

An inhaler article includes a body extending along a longitudinal axis from a mouthpiece end to a distal end and a capsule cavity defined within the body. A mouthpiece air channel extends from the capsule cavity to the mouthpiece end. An end cap is disposed within the distal end and extends to the capsule cavity. The end cap extends from an end cap distal end to an end cap inner end. The end cap includes an air channel extending from the end cap distal end to the end
(Continued)

cap inner end. The air channel is non-parallel with the longitudinal axis.

20 Claims, 2 Drawing Sheets

(51) Int. Cl.
  *A24F 42/20* (2020.01)
  *A24F 42/60* (2020.01)
  *A24D 3/17* (2020.01)
  *A61K 31/465* (2006.01)
(52) U.S. Cl.
  CPC ...... *A61M 15/003* (2014.02); *A61M 15/0005* (2014.02); *A61M 15/0008* (2014.02); *A61M 15/06* (2013.01); *A61K 31/465* (2013.01); *A61M 2202/064* (2013.01); *A61M 2206/16* (2013.01)
(58) Field of Classification Search
  CPC ....... A24F 40/10; A24F 40/20; A61M 15/003; A61M 15/0008; A61M 15/0006; A61M 15/06; A61M 2202/064; A61M 2206/16
  See application file for complete search history.

(56) References Cited

U.S. PATENT DOCUMENTS

| | | | |
|---|---|---|---|
| 4,889,114 A | 12/1989 | Kladders | |
| 4,907,583 A * | 3/1990 | Wetterlin | A61M 11/002 128/203.15 |
| 4,995,385 A * | 2/1991 | Valentini | A61M 15/0041 128/203.23 |
| 5,441,060 A * | 8/1995 | Rose | A24F 42/60 131/271 |
| 5,727,546 A | 3/1998 | Clarke et al. | |
| 5,797,391 A | 8/1998 | Cook et al. | |
| 6,705,313 B2 | 3/2004 | Niccolai | |
| 2002/0073997 A1 | 6/2002 | Keane et al. | |
| 2003/0094173 A1 * | 5/2003 | Burr | A61M 15/0028 128/200.23 |
| 2004/0206350 A1 | 10/2004 | Alston et al. | |
| 2006/0254583 A1 | 11/2006 | Deboeck et al. | |
| 2007/0221216 A1 * | 9/2007 | Ganem | A61M 15/0028 128/203.12 |
| 2011/0048414 A1 * | 3/2011 | Hoekman | A61M 15/00 128/200.23 |
| 2011/0297166 A1 * | 12/2011 | Takeuchi | A24F 42/60 131/274 |
| 2012/0000480 A1 * | 1/2012 | Sebastian | A24D 3/068 131/332 |
| 2013/0327327 A1 | 12/2013 | Edwards et al. | |
| 2015/0027468 A1 | 1/2015 | Li et al. | |
| 2015/0136132 A1 | 5/2015 | Papania et al. | |

FOREIGN PATENT DOCUMENTS

| | | |
|---|---|---|
| JP | 2006522663 | 10/2006 |
| RU | 2067876 C1 | 10/1996 |
| RU | 125433 U1 | 3/2013 |
| RU | 143972 U1 | 8/2014 |
| RU | 2328192 C1 | 7/2018 |
| WO | 20040091705 | 10/2004 |
| WO | WO 2015/166350 A2 | 11/2015 |
| WO | 20150193498 | 12/2015 |
| WO | 20160168266 | 10/2016 |

OTHER PUBLICATIONS

International Search Report and Written Opinion for PCT/IB2017/057219, issued by the European Patent Office; dated Feb. 26, 2018:15 pgs.
International Preliminary Report on Patentability for PCT/IB2017/057219, issued by the European Patent Office; dated Nov. 2, 2019:20 pgs.
Extended European Search Report for EP 16201579.6, issued by the European Patent Office; dated Jan. 23, 2017; 8 pgs.
Hall, R.L. & Oser, B.L., "Recent Progress in the Consideration of Flavoring Ingredients under the Food Additive Amendments 3. GRAS substances," *Food Technology*, Feb. 1965: p. 151-197.
Cohen et al., "GRAS Flavoring Substances," 27. *GRAS Flavoring Substances. Food Technology for Flavoring Extract Manufacturers Association*, Aug. 2015:69(8):40-59.
Japanese Office Action issued for JP 2019-528805 by the Japanese Patent Office; dated Sep. 8, 2021: 4 pgs. including English Translation.

* cited by examiner

INHALER WITH SWIRL END PLUG

This application is the § 371 U.S. National Stage of International Application No. PCT/IB2017/057219, filed 17 Nov. 2017, which claims the benefit of European Application No. 16201579.6, filed 30 Nov. 2016, the disclosures of which are incorporated by reference herein in their entireties.

This disclosure relates to an inhaler article that includes an air inlet channel that extends through an end cap. The air inlet channel may induce a swirling airflow within the inhaler article.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose in a single breath.

It would be desirable to provide a nicotine powder inhaler that provides nicotine particles to the lungs at inhalation or air flow rates that are within conventional smoking regime inhalation or air flow rates. It would also be desirable to provide deliver the nicotine powder inhaler with an inhaler article that has a form similar to a conventional cigarette. It would also be desirable to provide an inhaler article that is simple to manufacture and convenient to use by a consumer.

This disclosure is directed to an inhaler article comprising a body extending along a longitudinal axis from a mouthpiece end to a distal end. A capsule cavity is defined within the body. A mouthpiece air channel extends from the capsule cavity to the mouthpiece end. An end cap is disposed within the distal end and extends to the capsule cavity. The end cap extends from an end cap distal end to an end cap inner end. The end cap includes an air channel extending from the end cap distal end to the end cap inner end. The air channel is non-parallel with the longitudinal axis.

The one or more airflow channels through the end cap may initiate "swirling" air flow though the capsule cavity. The swirling air flow may cause a capsule contained within the capsule cavity to rotate and release nicotine particles (once pierced) into the airflow through the inhaler article. Preferably there may be more than one airflow channel through the end cap. The air channel may extend from the end cap distal end or distal end face, to the end cap inner end or inner end face. The air channel may extend the length of the end cap body. The end cap inner end may define the distal end of the capsule cavity. The air channel may extend from the end cap distal end or distal end face, to the end cap inner end or inner end face and define a curved or arcuate path.

Advantageously, providing the air channel along the length of the end cap provides an inhaler article that has a form similar to a conventional cigarette and an airflow configuration that is similar to a conventional cigarette. Advantageously, this inhaler article is simple to manufacture and convenient to use.

The end cap may include a piercing channel extending along the end cap longitudinal length. A resealable element may be disposed at either end of the piercing channel. The piercing channel may be co-axial with the longitudinal axis.

Advantageously, providing a piercing channel along the end cap allows reliable piercing of a capsule contained within the capsule cavity. Advantageously, the resealable element maintains the integrity of the desired air flow pattern within the capsule cavity.

A porous support element may separate the capsule cavity from the mouthpiece end. The porous support element may be a filter element. Airflow from the capsule cavity may flow through the porous support element to the mouthpiece end.

Advantageously, the porous support element allows entrained dry powder particles to freely pass through the porous support element while maintaining the physical dimensions of the capsule cavity. Advantageously, the porous support element may be a filter element that may be similar to a conventional plug of filter material utilized in conventional cigarettes. Advantageously, the porous support element may improve the desired air flow pattern through the capsule cavity.

The inhaler article described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler may have a form similar to a conventional cigarette and may mimic the ritual of conventional smoking. This inhaler may be simple to manufacture and convenient to use by a consumer.

Air flow management through the capsule cavity may cause the capsule to rotate during inhalation and consumption. The capsule contains nicotine particles comprising nicotine (also referred to as "nicotine powder" or "nicotine particles") and optionally particles comprising flavour (also referred to as "flavour particles"). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology August 2015 pg. 40-59, and intervening GRAS Flavoring Substances publications 4 to 26. For the purpose of this disclosure, nicotine is not considered as a flavourant or flavour.

The inhaler article described herein may be combined with a piercing element or piercing device to deliver the nicotine particles to a consumer. The piercing element or piercing device may be separated from or not form a portion of the inhaler article. A plurality of these inhaler articles may be combined with a piercing element or piercing device to form a kit.

An inhaler article includes a body extending along a longitudinal axis from a mouthpiece end to a distal end and a capsule cavity defined within the body. A mouthpiece air channel extends from the capsule cavity to the mouthpiece end. An end cap is disposed within the distal end and extends to the capsule cavity. The end cap extends from an end cap distal end to an end cap inner. An air channel extends from the end cap distal end to the end cap inner end. The air channel is non-parallel with the longitudinal axis along at least a portion of the length of the air channel.

The end cap defines a body extending along a longitudinal axis from an end cap distal end or distal end face, to the end cap inner end or inner end face. The end cap inner end may define the distal end of the capsule cavity.

The air channel may extend from the end cap distal end or distal end face, to the end cap inner end or inner end face. The air channel may extend the length of the end cap body. The air channel may extend from the end cap distal end or distal end face, to the end cap inner end or inner end face and define a curved or arcuate path. The air channel may extend from the end cap distal end or distal end face, to the end cap inner end or inner end face and define a curved or arcuate path along an outer surface of the end cap body.

The inhaler body may resemble a smoking article or cigarette in size and shape. The inhaler body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body. The inhaler body may have an outer diameter in a range from about 6 mm to about 10 mm, or from about 7 mm to about 10 mm, or about 7 mm to about 9 mm, or about 8 mm. The inhaler body may have a length (along the longitudinal axis) in a range from about 40 mm to about 90 mm, or from about 50 mm to about 80 mm, or about 60 mm to about 70 mm, or 65 mm.

The air channel may be configured to induce a swirling air flow pattern within the capsule cavity of the inhaler body. The air channel may draw inlet air into the capsule cavity of the inhaler body from the end cap distal end. The air channel may induce rotational air flow or swirling air flow as the air flows through the air channels and through the capsule cavity. Air flow through the inhaler device preferably enters the inhaler device at the distal end face or end cap distal end of the inhaler device and moves along the longitudinal axis of the inhaler device to the mouthpiece end. An inlet of the air flow channel may be defined within the end cap distal end face. The end cap distal end face may be orthogonal to the longitudinal axis of the inhaler device. Air flow may not pass thorough the elongated body of the inhaler body. There may be no air inlets through the elongated body of the inhaler body.

The air channel may be continuously non-parallel with the longitudinal axis of the inhaler device along an entire length of the air channel. The air channel may be parallel along a portion of the length of the air channel and non-parallel along a remaining portion of the length of the air channel. The air channel may be parallel for a first portion or upstream portion of the air channel and be non-parallel for a second portion or downstream portion of the air channel exiting into the capsule cavity. The second portion may define a about 50% or less, or from about 5% to about 50%, or from about 10% to about 30% of the total air channel length.

The air channel may be a channel element defined along an outer surface of the end cap and extending along a length of the end cap. The end cap may define three sides of the air channel. The end cap may define a bottom surface and opposing depth sides that define a depth of the air channel. The end cap may be inserted into the distal end of the inhaler body and form a portion of the distal end of the inhaler body.

The distal end of the inhaler body may surround at least about 75%, or at least about 85% or at least about 90% or 100% of the length of the end cap. The distal end of the inhaler body may contain and hold the end cap in place within the distal end of the inhaler body.

The end cap may be inserted into the distal end of the inhaler body and may be fixed to the inhaler body by friction fit or an adhesive, for example. A distal end portion of the inhaler body may cooperate with the end cap air channel to enclose the air channel or form the remaining top surface of the air channel. The top surface may oppose the bottom surface defined by the end cap. The top surface and bottom surface may be parallel to each other. The opposing depth sides may be parallel to each other. The opposing top surface and bottom surface may be orthogonal to the opposing depth sides.

The air channel may extend a distance along an arc that is co-axial with the longitudinal axis. The air channel may be curved with respect the longitudinal axis of the inhaler device. The air channel may rotate around the circumference of the end cap as a function of a location along the end cap length. The air channel may rotate around about 5% to about 100%, or about 25% to about 50% of the circumference. The air channel may rotate around the circumference of the end cap an arc length (distance when viewing the end cap from the distal end face) having a central angle (that may be coincident with the longitudinal axis of the inhaler body) in a range from about or from about 5 degrees to about 360 degrees, or about 45 degrees to about 180 degrees, or from about 45 degrees to about 135 degrees.

The air channel may enter the capsule cavity at an angle relative to the longitudinal axis. The air channel may enter the capsule cavity at an angle in a range from about 5 degrees to about 89 degrees, or about 45 degrees to about 89 degrees, or about 60 degrees to about 89 degrees, or about 70 degrees to about 88 degrees. The air channel may have a first portion parallel with the longitudinal axis and a second portion exiting into the capsule cavity at an angle relative to the longitudinal axis as described above.

The air channel may include at least two, or two or more air channels formed into the end cap. The air channel may include at least three, or three or more air channels formed into the end cap. The air channels may be located symmetrically about the end cap. The air channels may oppose each other about the end cap along the end cap length. The one or more air channels may have a helical shape (forming a portion of a spiral). The helical air channels may be symmetrically disposed along the end cap length and preferably oppose each other along the end cap length. The air channels may each extend a distance along an arc that are each co-axial with the longitudinal axis. The inhaler body may form the top surface for each air channel.

The end cap and air channel defined thereon may be precisely designed and manufactured to impart the desired air flow pattern through the capsule cavity of the inhaler device. This inhaler body and end cap may form a separate piece assembly that may provide for a simple and reliable manufacture and performance of the inhaler device.

The end cap may have an end cap length in a range from about 3 mm to about 12 mm, or from about 4 mm to about 10 mm, or from about 5 mm to about 9 mm, or about 7 mm. The end cap may have an outer diameter sufficient to form a close or friction fit with the inner diameter of the inhaler body. The end cap may have an outer diameter in a range from about 5 mm to about 10 mm, or from about 6 mm to about 9 mm, or about 6.5 mm to about 8.5 mm, or about 7.5 mm.

The end cap may include a collar element having a larger diameter than the remaining body of the end cap. The collar element may function as a physical stop to ensure proper placement of the end cap within the distal end portion of the elongated inhaler body. The collar may abut the elongated inhaler body. The collar may have a diameter that is about 0.5 mm to about 1 mm greater than the diameter than the remaining body of the end cap. The collar element may have a diameter that is substantially similar or the same as the outer diameter of the elongated inhaler body.

The end cap may include a linear piercing channel extending through the length of the end cap. The linear piercing channel may extend along a central axis of the end cap. The linear piercing channel may be co-axial with the longitudinal axis of the inhaler body. The linear piercing channel may be sized to allow a piercing element to pass through the linear piercing channel. The a linear piercing channel may have a diameter in a range from about 0.5 mm to about 2 mm.

The end cap may include a resealable element disposed on or within the linear piercing channel. The linear piercing channel includes a first end forming a portion of the end cap distal end and an opposing second end forming a portion of the end cap inner end. The resealable element may be disposed on or within end cap inner end. Alternatively or in addition, the resealable element may be disposed on or within the end cap distal end.

The resealable element may seal the linear piercing channel. The resealable element may form a hermetic or airtight seal or barrier along the linear piercing channel. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like.

The capsule cavity may define a cylindrical space configured to contain a capsule (that may have an obround shape). The capsule cavity may have a length of about at least 110% to less than about 200% of a length of the capsule contained therein. The capsule cavity may have a substantially uniform or uniform diameter along the length of the capsule cavity. The capsule cavity may have a substantially cylindrical or cylindrical cross-section along the length of the capsule cavity. The capsule cavity may have a uniform diameter along the length of the capsule cavity that is from about 101% to about 125%, or from about 105% to about 110% of the outer diameter of the capsule contained within the capsule cavity. The configuration of the capsule cavity may allow the capsule to rotate with stability within the capsule cavity. The longitudinal axis of the capsule may rotates with stability about the longitudinal axis of the inhaler body during inhalation. The length of the capsule cavity may form an airtight barrier.

The capsule cavity may be bounded on an upstream side by the end cap and bounded on a downstream side by a porous support element. The end cap and porous support element cooperate to contain the capsule longitudinally within the capsule cavity. The porous support element may fill the inner diameter of the elongated inhaler body. The porous support element may allow air flow to exhibit a uniform airflow along the cross-section of the elongated inhaler body through the porous support element. The porous support element may function as a diffuser to reduce turbulence effects or edge effects and ensure or maintain the desired air flow pattern through the capsule cavity.

The porous support element may have a length that extends along the longitudinal axis a distance from about 20 mm to about 40 mm, or from about 22 mm to about 35 mm, or from about 25 mm to about 30 mm, or about 27 mm. The porous support element may have an outer diameter sufficient to form a friction fit with the inner diameter of the inhaler body. The porous support element may have an outer diameter in a range from about 5 mm to about 10 mm, or from about 6 mm to about 9 mm, or about 6.5 mm to about 8.5 mm, or about 7.5 mm.

The porous support element may define a filter element. The filter element may be formed of a network of fibres. The network of fibres may be a nonwoven fibre element. The porous support element may be a plug of filtration material. Fibres forming the porous support element may be derived from polylactic acid. Fibres forming the porous support element may be cellulose acetate. The filter element may be a plug of cellulose acetate or a plug of polylactic acid. The porous element may comprise a plastic mesh. The plastic mesh may have holes of from about 1 $mm^2$ to about 4 $mm^2$ or of about 2 $mm^2$.

A system may include an inhaler article as described herein, and a capsule disposed within the capsule cavity of the inhaler article. The capsule may contain particles comprising nicotine. The capsule cavity may have a shape similar to the shape of the capsule. The capsule cavity may have a circular cross-sectional shape and a first diameter and the capsule may have a second diameter being less than the first diameter. The second diameter may be in a range from about 80% to about 99% of the first diameter, or the second diameter may be in a range from about 90% to about 98% of the first diameter. The capsule cavity may have a length of about 20 mm and an inner diameter of about 6.6 mm when containing a capsule size 3 flat. The cavity may have a length of about 24 mm and an inner diameter of about 7.7 mm when containing a capsule size 1 flat.

The capsule may be sealed within the inhaler article prior to consumption. The inhaler article may be contained within a sealed or airtight container or bag. The inhaler article may include one or more peelable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

A separate piercing element, such as a metal or rigid needle, may form a single aperture through the capsule received in the capsule cavity. The piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles"). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 10 micrometres or less, or 5 micrometres or less, or in a range from about 1 micrometre to about 3 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include flavour particles. The flavour particles may have any useful size distribution for inhalation delivery selectively into the mouth or buccal cavity of a user.

The powder system may have at least about 40%, or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about. 50 micrometres or greater. The powder system may have at least about 40% or at least about 60%, or at least about 80%, by weight of the flavour of the powder system comprised in particles having a particle size in a range from about 50 micrometre to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Figure 1:
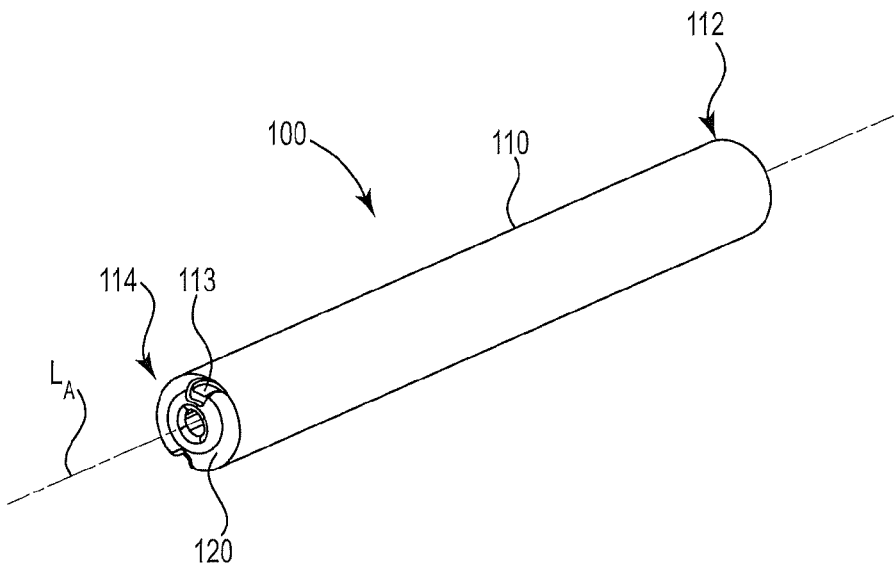
FIG. 1 is a perspective view of an illustrative inhaler article.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
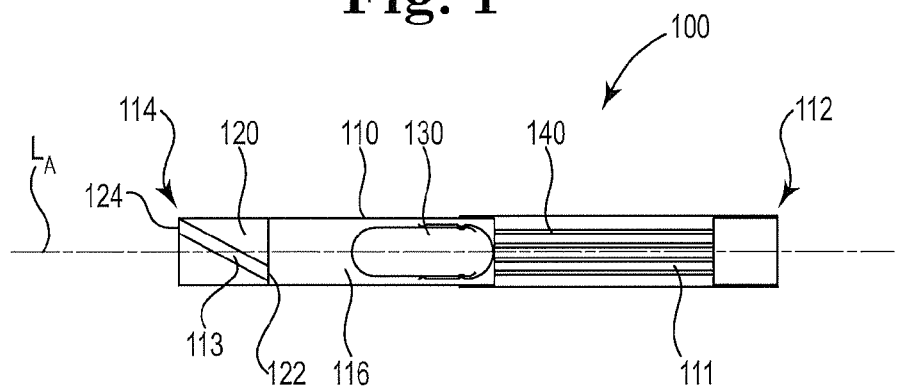
FIG. 2 is a cross-sectional schematic diagram of the illustrative inhaler article of FIG. 1 along the longitudinal axis.

FIG. 1 and FIG. 2 illustrate an exemplary inhaler article 100. FIG. 2 is a cross-sectional schematic diagram of the illustrative inhaler article of FIG. 1 along the longitudinal axis. The inhaler article 100 includes a body 110 extending along a longitudinal axis LA from a mouthpiece end 112 to a distal end 114 and a capsule cavity 116 defined within the body 110. A mouthpiece air channel 111 extends from the capsule cavity 116 to the mouthpiece end 112. An end cap 120 is disposed within the distal end 112 and extends to the capsule cavity 116. The end cap 120 extends from an end cap distal end 124 to an end cap inner end 122. The end cap 120 includes an air channel 113 extending from the end cap distal end 124 to the end cap inner end 122. The air channel 113 is non-parallel with the longitudinal axis LA.

The air channel 113 extends from the end cap distal end or distal end face 124, to the end cap inner end or inner end face 122. The air channel 113 extends the length of the end cap body 123. The end cap inner end or inner end face 122 defines the distal end of the capsule cavity 116. The air channel 113 extends from the end cap distal end or distal end face 124, to the end cap inner end or inner end face 122 and defines a curved or arcuate path along an outer surface of the end cap body 123.

The end cap inner end 122 and a porous support element 140 bound the capsule cavity 116. A capsule 130 is disposed within the cavity 116. The capsule 130 contains particles comprising nicotine. The end cap 120 and the porous support element 140 cooperate to contain the capsule 130 longitudinally within the capsule cavity 116. The mouthpiece end 112 is illustrated having a recessed end where the body 110 bounds an open space at the mouthpiece end 112. Alternatively the porous support element 140 can extend to the mouthpiece end 112 to fill the entire mouthpiece end 112.

FIG. 3A to FIG. 4B illustrate opposing curved, or helical air channels 113 rotating about the circumference as a function of a location along the length of the end cap 120. The end cap 120 may include a collar element 125 having a larger diameter than the remaining body 123 of the end cap 120.

FIG. 3A, FIG. 4A, FIG. 5 and FIG. 6 illustrate a linear piercing channel 121 extending through the length of the end cap 120. The linear piercing channel 121 may extend along a central axis of the end cap 120.

Figures 3A, 3B, 4A, 4B:
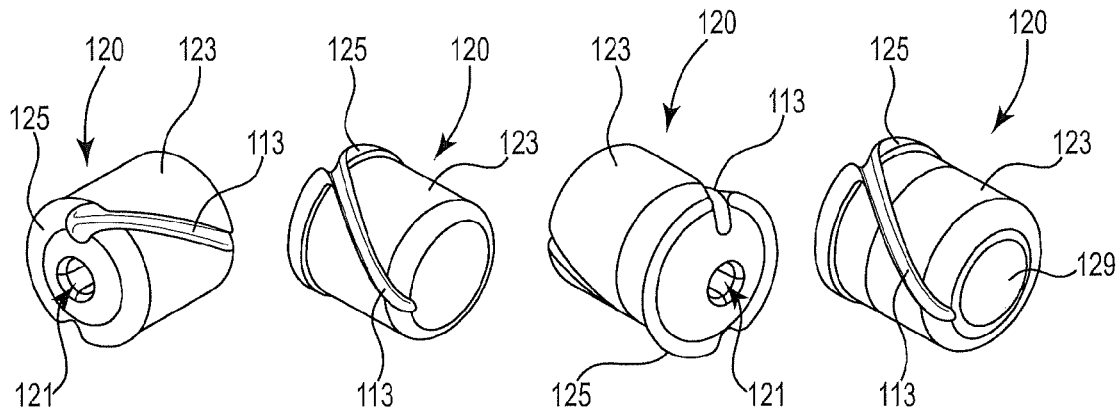
FIG. 3A and FIG. 3B are perspective views of an illustrative end cap.
FIG. 4A and FIG. 4B are perspective views of another illustrative end cap.
Figure 5:
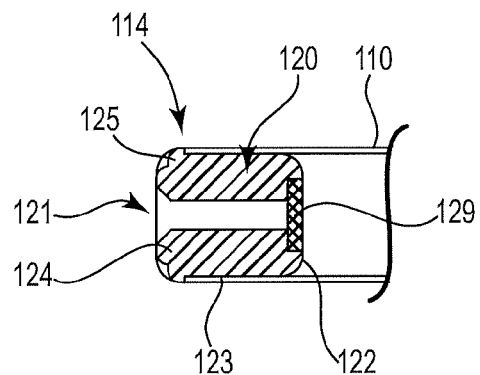
FIG. 5 is a cross-sectional schematic diagram of another illustrative end cap.
Figure 6:
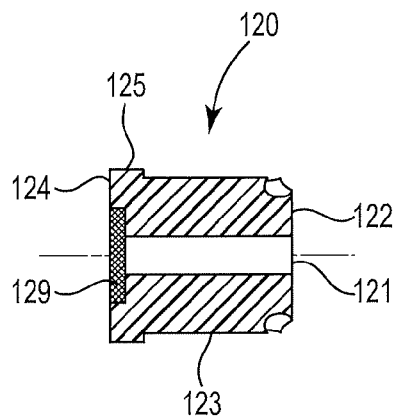
FIG. 6 is cross-sectional schematic diagram of another illustrative end cap.

FIG. 4B, FIG. 5 and FIG. 6 illustrate a resealable element 129 disposed on or within the linear piercing channel 121. FIG. 4B and FIG. 5 illustrate a resealable element 129 disposed on the end cap inner end 122 and sealing the linear piercing channel 121. FIG. 6 illustrates a resealable element 129 disposed on the end cap distal end 124 and sealing the linear piercing channel 121.

A separate piercing element (not shown) may be utilized by a consumer to pierce the resealable element 129 along the linear piercing channel 121 and puncture the capsule 130 contained within the capsule cavity 116. The piercing element may be withdrawn from the inhaler article 100 to reseal the resealable element 129. A consumer may then utilize the inhaler device.

The invention claimed is:

1. An inhaler article comprising:
    a body extending along a longitudinal axis from a mouthpiece end to a distal end;
    a capsule cavity defined within the body;
    a mouthpiece air channel extends from the capsule cavity to the mouthpiece end; and
    an end cap inserted into the distal end and extending to the capsule cavity, the end cap extending from an end cap distal end face to an end cap inner end, the end cap inner end defining a distal end of the capsule cavity, and the end cap comprising an air channel extending from the end cap distal end face to the end cap inner end, the air channel being non-parallel with the longitudinal axis;
    wherein the air channel extends a distance along an arc that is co-axial with the longitudinal axis.

2. The inhaler article according to claim 1, wherein the air channel is curved with respect the longitudinal axis and rotates around a circumference as a function of a location along a length of the end cap.

3. The inhaler article according to claim 2, wherein the air channel rotates around about 25% to about 50% of the circumference.

4. The inhaler article according to claim 1, wherein the air channel comprises at least two air channels that are symmetrical and opposing each other along the end cap length.

5. The inhaler article according to claim 1, wherein the air channel comprises at least two helical air channels that are symmetrical and each extend a distance along an arc that are co-axial with the longitudinal axis and oppose each other along the end cap length.

6. The inhaler article according to claim 1, wherein the end cap comprises a linear piercing channel and a resealable element disposed on or within the linear piercing channel and the linear piercing channel is co-axial with the longitudinal axis.

7. The inhaler article according to claim 6, wherein the linear piercing channel has a first end forming a portion of the end cap distal end and an opposing second end forming a portion of the end cap inner end, and the resealable element is disposed on or within the end cap inner end.

8. The inhaler article according to claim 6, wherein the linear piercing channel has a first end forming a portion of the end cap distal end and an opposing second end forming a portion of the end cap inner end, and the resealable element is disposed on or within the end cap distal end.

9. The inhaler article according to claim 6, wherein the resealable element is a septum.

10. The inhaler article according to claim 1, further comprising a filter element disposed within the body and separating the capsule cavity from the mouthpiece end, the filter element in air flow communication with the capsule cavity and the mouthpiece air channel.

11. The inhaler article according to claim 10, wherein the filter element comprises fibres derived from polylactic acid.

12. The inhaler article according to claim 1, wherein the body has an outer diameter that is substantially constant from the distal end to the mouthpiece end, the outer diameter being in a range from about 7 mm to about 10 mm.

13. A system comprising;
an inhaler article according to claim 1; and
a capsule disposed within the capsule cavity of the inhaler article.

14. The system of claim 13, wherein the capsule contains particles comprising nicotine.

15. An inhaler article comprising:
a body extending along a longitudinal axis from a mouthpiece end to a distal end;
a capsule cavity defined within the body;
a mouthpiece air channel extends from the capsule cavity to the mouthpiece end; and
an end cap inserted into the distal end and extending to the capsule cavity, the end cap extending from an end cap distal end face to an end cap inner end, the end cap inner end defining a distal end of the capsule cavity, and the end cap comprising an air channel extending from the end cap distal end face to the end cap inner end, the air channel being non-parallel with the longitudinal axis;
wherein the air channel is curved with respect to the longitudinal axis and rotates around a circumference as a function of a location along a length of the end cap.

16. The inhaler article according to claim 15, wherein the air channel rotates around about 25% to about 50% of the circumference.

17. The inhaler article according to claim 15, wherein the air channel comprises at least two helical air channels that are symmetrical and each extend a distance along an arc that are co-axial with the longitudinal axis and oppose each other along the end cap length.

18. The inhaler article according to claim 15, wherein the end cap comprises a linear piercing channel and a resealable element disposed on or within the linear piercing channel and the linear piercing channel is co-axial with the longitudinal axis.

19. The inhaler article according to claim 15, wherein the air channel comprises at least two air channels that are symmetrical and opposing each other along the end cap length.

20. The inhaler article according to claim 15, wherein the body has an outer diameter that is substantially constant from the distal end to the mouthpiece end, the outer diameter being in a range from about 7 mm to about 10 mm.

* * * * *